(12) United States Patent  
Rufer et al.

(10) Patent No.: US 8,936,572 B2  
(45) Date of Patent: Jan. 20, 2015

(54) AMBULATORY INFUSION DEVICE WITH ADVANCED BATTERY TESTING AND METHOD FOR TESTING A BATTERY

(71) Applicant: Roche Diagnostics International AG, Rotkreuz (CH)

(72) Inventors: Thomas Rufer, Ostermundigen (CH); Reto Aeschlimann, Aefligen (CH); Axel Remde, Luetzelflueh (CH)

(73) Assignee: Roche Diagnostics International AG, Rotkreuz (CH)

( * ) Notice: Subject to any disclaimer, the term of this patent is extended or adjusted under 35 U.S.C. 154(b) by 147 days.

(21) Appl. No.: 13/826,607

(22) Filed: Mar. 14, 2013

(65) Prior Publication Data

US 2013/0214787 A1    Aug. 22, 2013

Related U.S. Application Data

(62) Division of application No. 12/977,403, filed on Dec. 23, 2010, now Pat. No. 8,585,647.

(30) Foreign Application Priority Data

Dec. 28, 2009    (EP) .................................... 09016039

(51) Int. Cl.
*A61M 37/00* (2006.01)
*G01N 27/416* (2006.01)
*G01R 31/36* (2006.01)
*A61M 5/142* (2006.01)

(52) U.S. Cl.
CPC ....... *G01R 31/3606* (2013.01); *A61M 5/14244* (2013.01); *A61M 5/14276* (2013.01)
USPC .......................................... 604/131; 324/430

(58) Field of Classification Search
USPC ........................................................ 604/131
See application file for complete search history.

(56) References Cited

U.S. PATENT DOCUMENTS

| | | | |
|---|---|---|---|
| 4,345,603 A * | 8/1982 | Schulman | ........................ 607/29 |
| 5,904,707 A | 5/1999 | Ochs et al. | |
| 8,164,307 B2 * | 4/2012 | Cargonja et al. | .............. 320/132 |

(Continued)

FOREIGN PATENT DOCUMENTS

| | | |
|---|---|---|
| EP | 1 619 512 A2 | 1/2006 |
| EP | 1 887 544 A1 | 2/2008 |
| WO | 2008/129549 A1 | 10/2008 |

OTHER PUBLICATIONS

Extended European Search Report, Appln. No. EP09016039, Aug. 11, 2010, 5 pages.

*Primary Examiner* — Jason Flick  
(74) *Attorney, Agent, or Firm* — Dinsmore & Shohl LLP

(57) ABSTRACT

Included are embodiments of an ambulatory infusion device. Some embodiments include a battery receiving portion that receives a user-replaceable battery of variable individual characteristics. The user-replaceable battery may serve as a primary power source of the ambulatory infusion device and being successively depleted during application. Similarly, some embodiments include a dosing unit with an electrically powered actuator and an electronic controller that controls operation of the ambulatory infusion device. Still some embodiments include a testing unit that is operatively coupled to the electronic controller, the testing unit being designed to carry out a battery test, the battery test including determining an off-circuit voltage and an internal resistance of the user-replaceable battery. Still some embodiments include an alerting unit that is operatively coupled to the testing unit and/or the electronic controller to provide an alert to a device user in dependence of a battery test result.

16 Claims, 10 Drawing Sheets

(56) References Cited

U.S. PATENT DOCUMENTS

2008/0015644 A1   1/2008   Julian et al.
2008/0269724 A1   10/2008  Sarkinen et al.
2009/0209945 A1   8/2009   Lobl et al.
2010/0087778 A1* 4/2010   Genosar et al. .................. 604/65

* cited by examiner

AMBULATORY INFUSION DEVICE WITH ADVANCED BATTERY TESTING AND METHOD FOR TESTING A BATTERY

CROSS-REFERENCE TO RELATED APPLICATION

This application is a divisional application of U.S. patent application Ser. No. 12/977,403 filed Dec. 23, 2010, the entire disclosure of which is hereby incorporated herein by reference.

TECHNICAL FIELD

The present disclosure is related to ambulatory infusion devices including a testing unit for testing a battery of the devices and to corresponding battery testing methods.

BACKGROUND

External ambulatory infusion devices for the infusion of a liquid drug over an extended time period may be used for a number of therapies. In particular, such devices form the basis for a therapy of Diabetes Mellitus by CSII (Continuous Subcutaneous Insulin Infusion). An ambulatory infusion device is designed to provide a basal drug supply substantially continuously night and day in accordance with a time-variable basal infusion schedule and is further designed to administer larger drug boli in a short time period on demand. The device is typically designed to be carried substantially continuously over an extended time period of typically several months up to several years.

In the following, an external ambulatory infusion device according to the technical field as stated above and in particular an ambulatory infusion device in accordance with the present disclosure is referred to as "device". Besides diabetes therapy, those devices may be used for a number of further therapies, such as cancer treatment or pain therapy, without requiring substantial modification.

Such devices are typically powered by one or multiple energy storages, in particular rechargeable or non-rechargeable batteries. Several single batteries may typically be connected in series, thus forming an overall battery of higher voltage. Alternatively or additionally, several batteries may be provided for dedicated purposes, such as one battery for powering the device under normal conditions and another battery as safety backup; one battery for powering the electronics and another one for powering the pump drive, or the like. In such configurations, the present disclosure may be applied to any or all of those different batteries.

Many existing ambulatory infusion devices are designed to repeatedly carry out a battery test. In such a battery test, the battery is connected to a test load for a short time period and the resulting terminal voltage is measured. In the following, a test load is generally assumed to be an Ohmic resistor, but it may also be complex, having an inductive and/or capacitive component. An alert is generated if the measured voltage is below a given threshold voltage. The testing interval between consecutive tests is typically in the range of some minutes.

SUMMARY

Included are embodiments of an ambulatory infusion device. Some embodiments include a battery receiving portion that receives a user-replaceable battery of variable individual characteristics. The user-replaceable battery may serve as a primary power source of the ambulatory infusion device and being successively depleted during application. Similarly, some embodiments include a dosing unit with an electrically powered actuator and an electronic controller that controls operation of the ambulatory infusion device. Still some embodiments include a testing unit that is operatively coupled to the electronic controller, the testing unit being designed to carry out a battery test, the battery test including determining an off-circuit voltage and an internal resistance of the user-replaceable battery. Still some embodiments include an alerting unit that is operatively coupled to the testing unit and/or the electronic controller to provide an alert to a device user in dependence of a battery test result.

BRIEF DESCRIPTION

In the following, exemplary embodiments of the disclosure are described with reference to the drawings.

DETAILED DESCRIPTION

Figure 1:
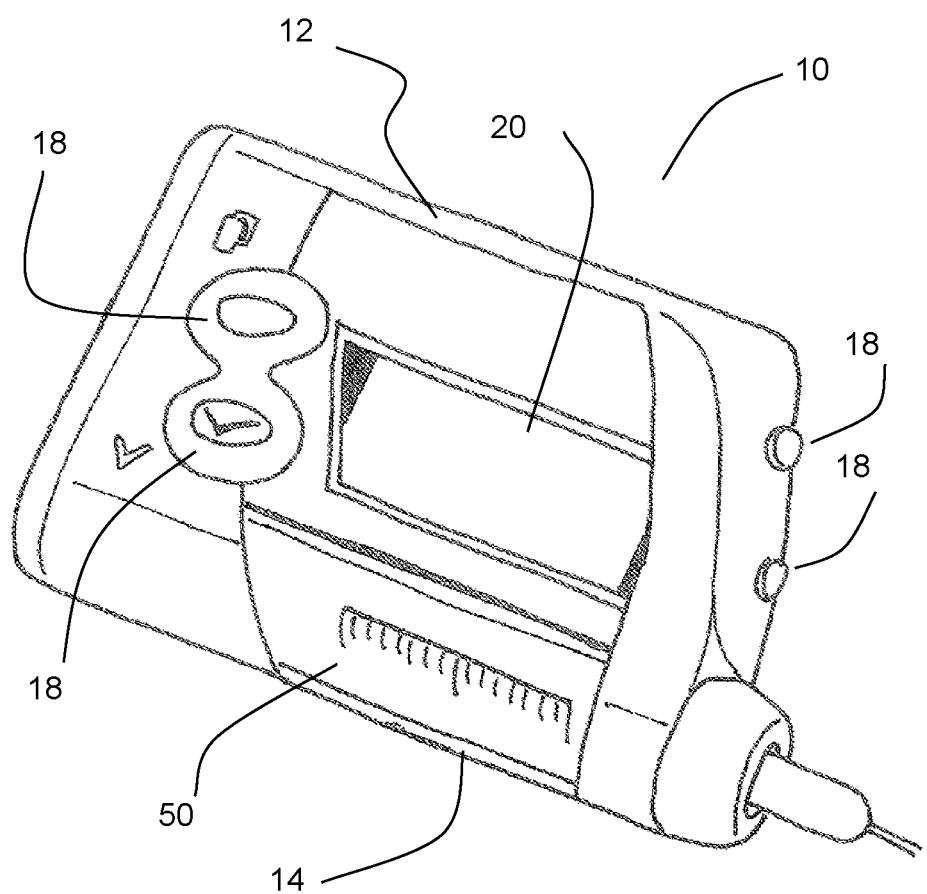
FIG. 1 shows an outside view of a device according to embodiments of the present disclosure.

Embodiments of the present disclosure may be configured to provide ambulatory infusion devices with improved battery testing capabilities. An ambulatory infusion device in accordance to the present disclosure may be designed to be carried by a user external of the body and concealed from view and for an extended time period.

The device may be configured to receive a user-replaceable battery of varying individual characteristics, the battery serving as primary power source of the infusion device and being successively depleted during application. In some embodiments, the battery is received by a dedicated battery compartment or battery receiving portion via a separate door or closure, such that the battery is accessible for the user without having to further open or to disassemble the device as such. The device may further include a dosing unit with an electrically powered actuator, an electronic controller, the controller controlling operation of the ambulatory infusion device.

The device may further include a testing unit, the testing unit being operatively coupled to the controller, the testing unit being designed to carry out battery tests. A battery test may include determining an off-circuit voltage and an internal resistance of the battery. Embodiments of the device may further include an alerting unit, the alerting unit being operatively coupled to the testing unit and/or an electronic controller or control circuitry of the device to provide an alert to a device user in dependence of a battery test result. As will be discussed below in more detail, an alert may especially be provided if a newly inserted battery is not suited for powering the device and/or if a battery is largely depleted.

By carrying out battery tests including determining the off-circuit voltage and the internal resistance of the battery, alert generation is adopted to the individual battery characteristics. As will be discussed below in more detail, the individual characteristics may include an initial off-circuit voltage and initial internal resistance. Additionally or alternatively, the individual characteristics may include depleting characteristics, that is, the change of various characteristics upon a battery being depleted. Besides the off-circuit voltage and the internal resistance, the individual characteristics may include further data, such as a maximum current that can be drawn from a battery, and, for a rechargeable battery, a minimum battery voltage without permanently damaging the battery.

Different or variable individual characteristics may result due to any of a number of reasons. In particular, differences may exist between batteries of different electrochemical designs, batteries manufactured by different processes and/or by different suppliers, batteries of different age when being used, and the like. In addition, some batch-to-batch variability as well as battery-to-battery variability is typically present, both of which may be significant in some cases. In the context of the present disclosure, the characteristics of batteries are considered as being "different" if the difference is large enough to require consideration with respect to the application of the battery and the generation of battery-related alerts.

At least two resistors may be provided that may serve as test loads. Similarly, in some embodiments, an electronically controlled load, such as variable resistor, for example a voltage controlled resistor, may be present in the testing unit. Control circuitry may be provided for selectively coupling the test load or one of several test loads to the battery. In combination with an evaluation and computation unit, the resistors and the voltage measurement unit serve as resistance measurement unit for determining the internal resistance and the off-circuit voltage of the battery. Designs of measurement units and corresponding testing methods will be discussed below in the context of exemplary embodiments.

When a load such as an Ohmic resistor is coupled to a battery, the voltage that can be measured at the battery terminals shows a step response in form of a downwards step in dependence of the internal resistance. The test load is favorably coupled to the battery for a time interval that is sufficiently long for the downwards step to be completed. For some batteries, this time interval is in the range of some milliseconds. Coupling the test load to a battery for a longer time interval consumes additional energy without and typically being associated with a corresponding benefit.

The dosing unit may include a spindle drive as currently used in many ambulatory infusion devices, such as a peristaltic pump head, a micro-membrane, a micro-piston pump, and/or the like. The actuator may include a motor, an electromagnet, piezzo-electric elements, and/or the like. The controller may include one or more microcontrollers and additional circuitry such as power circuitry for driving the actuator, memory and safety circuitry. The device may include further units such as a user interface and communication interfaces for the communication with external devices. These further units may be integral with or, fully or partly, separate from the device.

In the context of the present disclosure, the battery is considered as non-ideal battery, which includes an ideal battery, such as an ideal DC voltage supply, having an off-circuit-voltage, in series with an internal resistor having an internal resistance. The off-circuit voltage is the voltage that can be measured between the battery terminals when no current is drawn from the battery. In contrast, the terminal voltage is the voltage that can be measured at the battery terminals under normal operational conditions. When current is drawn from the battery, the terminal voltage is generally smaller as compared to the off-circuit voltage because of a voltage drop over the internal resistor. This voltage drop is defined according to Ohm's law by the internal resistance and the current that is drawn. The terminal voltage equals the off-circuit voltage if no current is drawn. This is the case, for example, if the voltage is measured with a voltage measurement unit of substantially infinite input resistance.

Figure 4:
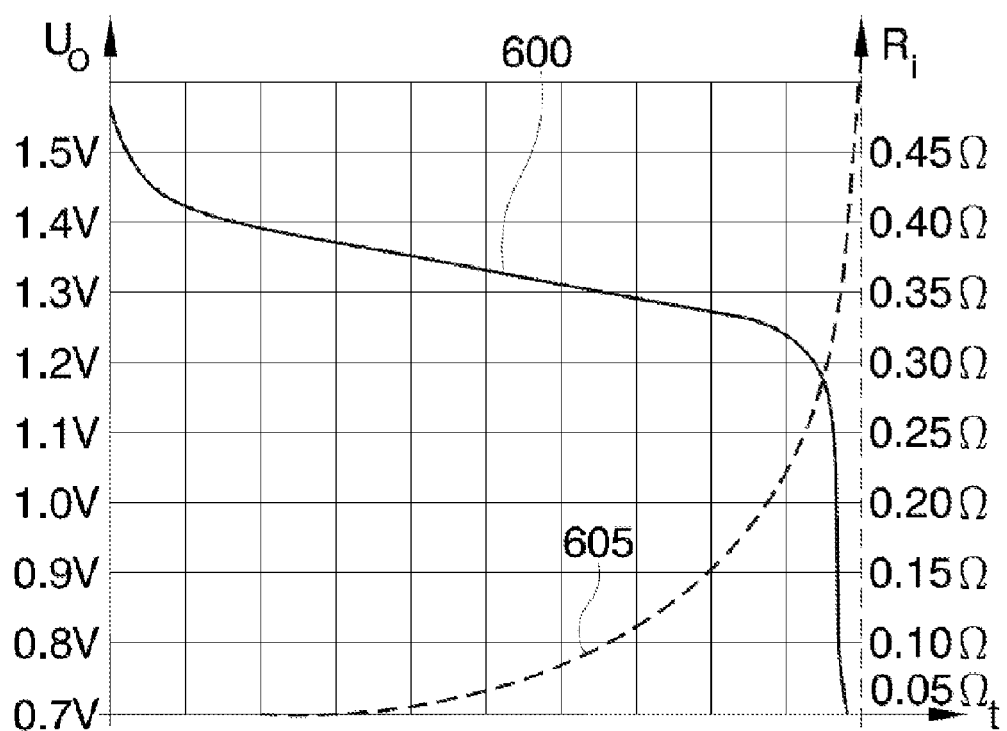
FIG. 4 shows an exemplary off-circuit voltage curve and a corresponding internal resistance curve of a battery in accordance with embodiments of the present disclosure.

When an energy storage such as a battery is being used, neither its off-circuit voltage nor its internal resistance is constant over time. The off-circuit voltage decreases and the internal resistance increases. Both effects reduce the terminal voltage if current is drawn. These effects are illustrated in FIG. 4, showing an exemplary off-circuit voltage $U_O$ curve 600 and the corresponding internal resistance $R_i$ curve 605 as measured over the usage time of a battery.

For batteries used in ambulatory infusion devices, distinct performance characteristics may be utilized for safe and reliable operation. Therefore, some devices are powered by special-purpose power packs that are especially designed to meet the device requirements. This approach, however, is accompanied by some drawbacks. In particular, the user has to stock those power packs and carry a number of them, for example when traveling. In addition, the price of the power packs is high because of the comparatively low production volume.

Some other devices are therefore designed to be powered by widely available general-purpose batteries, such as AA or AAA cells. Because of the variety of different electrochemical designs, manufacturing processes and qualities, however, not all of them are equally suited for powering the device. If an unsuitable battery is used, the device may spontaneously terminate operation without alerting the user.

This may especially occur if the voltage drops, during operation of the device, from a high level at which no alert would be generated to a very low level which is not sufficient for operating the device or the generation of an alert, with a steep drop of the terminal voltage and within and in a short time. Since the user is, in case of this event, not aware of the terminated infusion of the drug or substance, it may result in adverse effects.

This situation may occur because users are sometimes not aware that a particular battery may be unsuitable for powering the device as intended, even if the battery has the same dimensions and nominal voltage as a suitable battery and fits into the device. In some situations, such as when travelling into a foreign country, batteries having a labeling in a foreign and completely unknown language may be used such that the user does not know whether the battery is actually suitable. In addition, even generally suitable batteries in some cases show a defect or anomaly that may also cause untypically steep and unexpected voltage drops in a rather short time. In some further cases, a depleted battery is removed by the device user to be replaced and is subsequently inserted again rather than a fresh battery. It has been found that the suitability of a fresh, that is, unused, battery for powering the device can be determined based on its internal resistance and its off-circuit voltage. An ambulatory infusion device in accordance with the present disclosure may therefore be designed to execute a power-up routine following insertion of a battery, the power-up routine including carrying out a battery test, thus determining an initial internal resistance and an initial off-circuit voltage of the battery.

Based on these initial values, it can be determined if the inserted battery is generally suited for powering the device. In addition to testing the battery, the power-up routine may include further initialization and/or self-testing steps, such as checking the electrical integrity of the circuitry, testing components such as communication interfaces, device memory, user interfaces, and the like. The power-up routine may be carried out in a stop mode, a suspend mode or a service mode of the device, where no drug is infused into the user's body. After successfully carrying out the power-routine, the device may switch into a regular operation mode automatically or via a user command.

The phrase "regular operation mode" refers to a mode where the device carries out repeated and/or continuous drug administrations. An insulin pump as used for CSII is in such a regular operation mode administers an insulin dose every few minutes. A regular operation mode also includes the device operation between the administrations and may include further activities such as retracting a typically present spindle of the dosing unit when replacing a drug cartridge, powering a display backlight, providing alarms or alerts to the user or exchanging data with further devices.

The determined initial values may be stored in a device history, such as in a non-volatile memory that is also configured to store further data and events, such as carried-out administrations, the result of self-test routines, errors that occur during operation, and the like, favorably together with a time stamp. similar, the device may be configured to provide an alert to the device user if a battery test carried out during the power-up routine indicates that the battery is not suited for powering the device. A battery may especially not be suited for powering the device if its off-circuit voltage is too low and/or if its internal resistance is too high.

Providing an alert ensures that the user does not unintentionally insert a battery that is already largely depleted, defective, or generally unsuited, for example because of its electro-chemical design. The alert may for example be any of acoustic alert, such as via an acoustic transducer. Similarly, the alert may include a tactile alert, such as a pager vibrator. The alert may include an optical alert, such as a warning message on a device display.

In some embodiments, the device is designed such that it cannot switch to a regular operation mode if the inserted battery is unsuited, thus ensuring that a different and suited battery is used. Similarly, the device may be configured such that a warning is provided but the user may switch to a regular operation mode anyhow. This may be utilized in situations where a better-suited battery is not easily available, such as while traveling. By providing an alert, however, the user is made aware of the critical situation. Ways for determining, based on the internal resistance and the off-circuit voltage, whether or not a battery is suited for powering the device, will be discussed in more detail further below.

In some embodiments, the power-up routine includes assigning, based on the battery test, a stored battery type to the inserted battery. For this purpose, the device may store at least one characteristic initial off-circuit voltage and at least one characteristic initial internal resistance for a number of different battery types. The power-up routine may include assigning a battery type to the inserted battery based on comparison of determined and stored off-circuit voltage and internal resistance, respectively. Further, a battery type identifier is stored along with the characteristic data of the different battery types. The data are favorable stored as parameters in a non-volatile memory of the device, such as in form of a table.

The different battery types may in particular reflect different electrochemical designs, such as "Alkaline" (Al), Lithium" (Li), Zinc-Carbon" (ZC), "Nickel-Metal-Hybrid" (NiMh), each of which may be identified by its initial off-circuit voltage, its initial internal resistance, or a combination of both. The principle however, is not limited to these specific batteries technologies or the measured data. In particular ZC battery cells may be unsuited for powering many ambulatory infusion devices due to their high internal resistance and their depletion characteristics.

For the different battery types simply reflecting different electro-chemical designs, a battery type identifier may also reflect the electrochemical design, such as by its name. If batteries of the same general electro-chemical design exist that significantly differ with respect to their initial off-circuit voltage and/or initial internal resistance for other reasons, such as the manufacture process, they may also be considered as different battery types. The characteristic data may be stored in the device during initial configuration, such as at the manufacture site. However, the characteristic data may also be modified or updated later on, such as via a user interface or communication interface. This is favorable, for example, if a new type of battery becomes available. In a similar way, it may be used if a generally existing type of battery undergoes changes, for example due to a changed manufacturing process or a design change of the battery cell itself, which results in a change of the discharging characteristics, such as by introduction of a "chemical switch" or a current limiting device inside the battery.

In practice, ranges may be stored for the characteristic initial off-circuit voltage and the internal resistance rather than single values, the ranges reflecting individual variability, variability between manufacturers, and the like. Identification of a battery type is still possible if overlaps exist for different battery types for the initial off-circuit voltage or the internal resistance, as long as the combination of both is unique.

In some favorable embodiments, the device is designed to monitor a voltage of the battery during regular device operation and to provide an alert to the device user if the voltage of the battery falls below a predetermined threshold voltage. The monitored voltage may, for example be the off-circuit voltage or a terminal voltage with a defined test-load being connected to the battery. In some embodiments including battery voltage measurements during regular device operation, the power-up routine includes setting the predetermined threshold voltage in dependence of the assigned battery type. For this type of device, an adoption to the battery characteristics is automatically carried out or is suggested to the user after insertion of a new battery, while only the battery voltage needs to be subsequently monitored during regular operation.

Because of the different initial values as well as the different depletion characteristics, different alerting voltages are appropriate for different battery types, in particular for batteries of different electro-chemical design. In some embodiments, the device is configured to provide a pre-alert, that is, an early warning, a predetermined time before the battery voltage is critical, while the device is still operable. For a specific ambulatory infusion device that is powered by a single AA (LR6) battery cell, suited values are for example:

| Alkaline/Lithium: | Pre-alert: 1.175 V |
|---|---|
| | Alert: 1.100 V |
| NiMH rechargeable: | Pre-alert: 1.150 V |
| | Alert: 1.100 V |

In some favorable embodiment including an automated assignment of the assigned battery type, the ambulatory infusion device is designed to provide an indication of the assigned battery type to the device user. The indication is typically done via a device display, such as by displaying a stored battery type identifier. In some embodiments, the user information is provided for information purposes only. In some embodiments, the user may be allowed to manually override the assignment in case he is sure about the battery type and the automatic assignment is incorrect for some exceptional reason.

Both an automatically detected as well as a manually entered battery type of a newly inserted battery may be stored in an erasable but non-volatile memory, such as a device history. In some favorable embodiments, the device is designed to repeatedly carry out a battery test during regular device operation and is further designed, following a battery test during regular operation, to determine, based on the off-circuit voltage and the internal resistance as determined in the carried-out battery test, a capability of the battery for further powering the ambulatory infusion device, and for providing an alert to the device user in case of a lack of capability of the battery for further powering the ambulatory infusion device.

This type of embodiment may be configured to allow safe operation for a large range of battery types. The phrase "safe operation" refers to the device either operating as intended, in particular in a regular operation mode as discussed above, or terminating the infusion and alerting the user if operation as intended is not possible and/or cannot be ensured. For this type of embodiment, an initial assignment of the battery type in a power-up routine may be carried out but is not essential since the off-circuit voltage and the internal resistance, are substantially continuously monitored. Automatic adaption to the battery is achieved by the device providing an alert if the individual battery is not further capable of safely powering the device.

The favorable properties of this type of embodiment are be achieved based on the insight that the requirements with respect to the performance characteristics of a battery can be less tight as compared to prior art devices which generate an alert on the basis of a fixed voltage threshold. Fixed voltage thresholds require rather large safety margins which in many cases result in a battery being replaced considerably earlier than required.

As will become more readily apparent, the phrase "capability for powering the device" is used in the sense of a qualitative measure of the state of the battery. The capability is assumed to be maximal for a fresh and non-defective battery and is reduced over the usage time of the battery as it is depleted. For a non-ideal battery, the decreasing off-current voltage or terminal voltage as well as the increasing internal resistance over time reduce the capability of the battery for powering the device. The battery is assumed to be capable of powering the device if sufficient current can be drawn from the battery at a sufficiently high terminal voltage such that the device operates as intended.

If both the off-circuit voltage and the internal resistance are monitored during regular operation and serve, in combination, as basis for an alert generation, using or depleting the batteries individually to a large extent is enabled, thus allowing the usage of comparatively small batteries with an acceptable and sufficient battery lifetime. Such a device further allows safe operation of the device with batteries that are only partly suitable because they do not meet all characteristics that are normally required or desired for safely operating the device. This is particularly favorable in situations where a generally better battery is not easily available, such as when traveling.

In some embodiments, the testing unit is further configured to vary the battery testing in dependence of the capability of the battery for further powering the ambulatory infusion device. The testing may be varied by varying the time interval between consecutive tests, and, thus, the testing frequency, and/or by varying the testing stress that is exerted on the battery in each test. Varying the testing stress is associated with varying the current, power, and/or the energy that is drawn from the battery in a test. The testing is favorably varied such that the testing frequency and/or the testing stress are increased over the usage time of the battery. Increasing the testing frequency is similar to reducing the testing interval as the reciprocal of the testing frequency. Increasing the testing stress can be achieved by reducing the test load resistance or generally by increasing the current or power, respectively, that is drawn from the battery in a test.

Since each battery test is generally associated with some additional power consumption, each battery test reduces the battery lifetime. Therefore, the number of tests should generally not be larger than required. This allows avoiding the power consumption due to extensive testing at times when testing is less critical while carrying out sufficient testing where required, thus avoiding or reducing the drawbacks of current devices as discussed above.

In some embodiments that include varying the testing interval, the testing unit is designed to reduce the testing interval upon a decreasing voltage and/or upon an increasing internal resistance of the battery. This type of embodiment will be discussed in more detail below in the context of exemplary embodiments. The testing interval may especially be short if the voltage of the battery is low and/or the internal resistance of the battery is high, in order to ensure sufficient testing, especially when the battery approaches the end of its useful lifetime (see FIG. 4). The testing interval may be longer if the voltage is high and/or the internal resistance is low.

In some embodiments, the testing unit is configured to determine if the battery is capable of further powering the device by determining if the terminal voltage of the battery exceeds a reference voltage and/or by determining if a predetermined reference power can be drawn from the battery or determining if a predetermined reference current can be drawn from the battery.

In the following, the reference voltage is generally considered for illustrative purposes as a minimum voltage required for operating the device, the reference power is considered as a maximum power that may be drawn by the device and the reference current is a maximum current that may be drawn by the device. In practice, the reference values may be different and in particular include some safety margin both for general safety reasons and in order to ensure that the device can be safely operated for some further time after alerting the user, thus giving the user sufficient time of typically some hours up to some days to replace the battery.

For the battery to be capable of powering the device, a number of conditions should be met in dependence of the device design. In addition, different devices may show different characteristics with respect to the stress they exert on the battery. In particular, a device may, in a somewhat simplified model, be modeled as belonging to at least one of the following types:

Given resistance: The device is modeled as a resistor having a given load resistance, such that the current drawn from the battery as well as the terminal voltage of the battery can be determined from the load resistance in combination with the off-circuit voltage and the internal resistance of the battery in a straight-forward way by applying Ohm's law.

Given power: The device is modeled as drawing a given electrical power from the battery, with the resulting current drawn from the battery and the terminal voltage being determined by off-circuit voltage and the internal resistance of the battery.

Given current: The device is modeled as drawing a given current from the battery, largely independent from its terminal voltage and internal resistance.

While the actual load characteristics of the device may be more complex, these different device types provide a useful framework for the understanding and the practical implementation of the disclosure.

It should be noted that the term "given" refers to some defined reference operating conditions which may especially be such that the battery is maximally stressed, that is, a maximum current and/or power is drawn. The device circuitry, such as the actuator of the dosing unit, including microcontrollers and further components such as voltage converters require a minimum operating voltage.

With $U_0$ being the off-circuit voltage and $R_i$ being the internal resistance of the battery as determined by the testing unit, and $I_{max}$ being the maximum current that may be drawn by the device, the condition $$U = U_0 - R_i \cdot I_{max} \geq U_{min} \quad (1)$$

should be substantially met, with $U_{min}$ being the minimum operating voltage.

Besides the actuator of the dosing unit, a considerable current may be drawn by indicators, such as acoustic and/or tactile indicators, a display backlight and wireless communication interfaces, which may be present in the device and may therefore be considered for determining $I_{max}$.

If the device is modeled according to the given-current model, (1) may be used to determine whether the terminal voltage U is above the minimum operation voltage $U_{min}$. The testing unit may therefore be designed to determine the terminal voltage for the reference current $I_{max}$ as given by (1), to compare it with the minimum operating voltage $U_{min}$ and to activate the alerting unit if the condition given by (1) is not met.

If the device is modeled according to the given-resistance model with a given load resistance $R_L$, the corresponding condition to (1) is given by $$U = U_0 \cdot \left(1 - \frac{R_i}{R_i + R_L}\right) \geq U_{min}. \quad (2)$$

The device resistance is typically not constant but varies over time. For an insulin pump that is designed for pulsed administration with a small amount of insulin being administered every few minutes, the load resistance is particularly low, for example, during the administration and/or if a display backlight is switched on. It is rather high between the administrations if no further operations are carried out. The given load resistance $R_L$ is advantageously selected as the smallest resistance that is likely to occur during operation of the device.

For an energy storage, in particular a battery with a non-infinite internal resistance, the maximum power that can be drawn is limited and is drawn when the load resistance equals the internal resistance. Since the off-circuit voltage decreases and the internal resistance increases over the usage time of the battery as discussed above with reference to FIG. 4, the maximum power that can be drawn decreases. With $P_{max}$ being a the maximum power drawn by the device during normal operation, the condition $$\frac{U_0^2}{4R_i} \geq P_{max} \quad (3)$$

has therefore to be met for the battery to be capable for powering the device. In (3), the term on the left side corresponds to the power drawn by the internal resistor in the case of the device resistance being identical to the internal resistance.

If the device is modeled according to the given-power type, the testing unit may therefore be designed to determine the maximum power that can be drawn from the battery as given by the left side of (3), to compare it with the maximum power $P_{max}$ and to activate the alerting unit if the condition given by (3) is not met.

For the device being modeled according to the given-resistance type, the maximum power can be obtained via the relation $P = U^2/R_L$ in combination with (2). The testing unit may be designed to compute the power drawn by the device for a previously determined off-circuit voltage and internal resistance and to compare it with the maximum power that can be drawn from the battery according to (3).

For a device according to the given-power type, determining if the terminal voltage is above a minimum operation voltage $U_{min}$ cannot be carried out directly by evaluating (1) or (2) since neither of the current drawn by the device nor the load resistance is directly known. For the power $P = U \cdot I$ being given, the current I drawn from the battery as well as the terminal voltage U depend on the off-circuit voltage and the internal resistance. If the off-circuit voltage is high and the internal resistance is low, the current is low. With an increasing internal resistance and/or a decreasing off-current voltage, the current I increase accordingly. However, by applying $$U = U_0 - R_i \cdot I$$

$$p = U \cdot I \quad (4),$$

and (1), a quadratic equation $$U^2 - U \cdot U_0 + R_i \cdot P = 0 \quad (5)$$

may be obtained for U. The testing unit may therefore be designed to solve (5) for U either analytically or numerically using an approach according to the state of the art and to determine if the condition $$U \geq U_{min} \quad (6)$$

is met for $P = P_{max}$.

In addition to the above-given criteria, many batteries have a maximum threshold current that may be drawn. The testing unit may therefore be designed to compare the maximum current drawn by the device with the maximum threshold current or another reference current and activate the alerting unit if this current is exceeded. In some embodiments, the device includes a step-up voltage converter and the battery powers the device, at least in part, via the voltage converter.

For example, a motor serving as actuator in the dosing unit as well as some microcontrollers require a supply voltage that may be higher as compared to the battery voltage. The voltage converter may be configured as a DC/DC step-up converter, which provides a constant output voltage $U_2$ for an input voltage U being in a given range, with $U_2$>U. Such converters are commercially available and are favorable if the required operation voltage of the device is, at least in part, higher than the battery voltage. The battery may for example have a nominal voltage of 1.5V while further components of the device require a higher operation voltage, such as 3V, 5V, 6V or even higher.

A DC/DC step-up converter which is coupled to the terminals of the battery transforms the terminal voltage U and a current I on the input side to a voltage $U_2$ and a current $I_2$ on its output side such that $$U_2 \cdot I_2 = k \cdot U \cdot I$$

$$P_2 = k \cdot P \quad (7).$$

In (7), $P_2$ is the output power of the voltage converter, which may be the power for operating the device. P is the input power of the voltage converter, which may be the power that is drawn from the battery and k<1 is the converter efficiency. The output voltage $U_2$ is constant and the output current $I_2$ is given by the power consumption of the device. Accordingly, the output current $I_2$ assumes a maximum $I_{max}$ when the power consumption of the circuitry that is connected to the output side of the voltage converter assumes a maximum value $P_{2,max}$.

The voltage converter may require a minimum input voltage to operate as specified, with the input voltage of the voltage converter being the terminal voltage of the energy store. For some embodiments, the testing unit may therefore be designed to determine a terminal voltage of the battery at a reference power consumption level of the circuitry powered via the voltage converter and to compare the terminal voltage with a minimum operating voltage of the voltage converter. The terminal voltage may be determined by evaluating (5, 6) in combination with (7). In some embodiments, the device includes a prediction unit, the prediction unit being designed to predict a capability of the battery for further powering the device.

Predicting the capability of the battery for further powering the device may be utilized for providing an alert a given time before the battery may not be any longer capable for further powering the device. As discussed above, the capability for powering the device is largely dependent on the off-circuit voltage and the internal resistance of the battery. The prediction unit may therefore be coupled to the measurement unit and predict the course of the off-circuit voltage and the internal resistance based on previously determined values. The prediction may be carried out based on a number of extrapolation methods and algorithms, for example, by fitting a linear or quadratic function to a number of previously determined values. The future prediction time interval is favorably in a range of several hours, such as from 6 to 10 hours, in order to give the user sufficient time to replace the battery while the device is still operating as intended. A too long prediction interval, however, may be problematic due to the uncertainty of the extrapolation that results in the prediction uncertainty increasing with the prediction interval. The prediction may be updated each time a test is carried out.

The testing unit may be configured to determine the capability of the battery for further powering the device in addition or alternatively to determining off-circuit voltages and internal resistance values. In some embodiments, the ambulatory infusion device is configured to receive a standard general-purpose battery as power supply.

The phrase "general-purpose battery" refers to batteries that are widely available and used for a variety of electrics or electronics devices, such as electric torches, cameras, radios, pocket calculators, or the like. Many general-purpose batteries that may be used for powering an ambulatory infusion device are AA LR6, AAA LR03, or CR2032 batteries. Powering an ambulatory infusion device by such general-purpose batteries may allow for easily available and low cost replacements, such that the battery supply is typically no issue. As discussed above, however, a large variety exists, and not all batteries that appear to be equivalent with respect to their characteristics at a first glance actually are.

In a further aspect, the present disclosure is directed towards a method for testing a battery of an ambulatory infusion device, the ambulatory infusion device being designed to be carried by a user external of the body and concealed from view and for an extended time period. The battery is a user-replaceable battery of variable individual characteristics. The battery serves as primary power source of the ambulatory infusion device and is successively depleted during application. The method may include carrying out battery tests, a battery test including determining an off-circuit voltage and an internal resistance of the battery. The method may include providing an alert to a device user in dependence of a battery test result.

In some embodiments, the method includes executing a power-up routine following insertion of a battery into the ambulatory infusion device. In some embodiments, the power-up routine includes carrying out a battery test. Similarly, in some embodiments, the method may include carrying out a battery test during regular operation of the ambulatory infusion device (10), determining, based on the off-circuit voltage and the internal resistance as determined in the carried-out battery test, a capability of the battery for further powering the ambulatory infusion device, and providing an alert to the device user in case of a lack of capability of the battery (100) for further powering the device.

Additionally, as discussed herein, method blocks that are disclosed in conjunction with structural units such as devices may be used for detailing method claims which are based on other portions of the description. In the same manner, structural elements that are disclosed in conjunction with methods may be used for detailing structural claims.

Referring now to the drawings, FIG. 1 shows an outside view of an exemplary embodiment of an ambulatory infusion device 10 in accordance with the present disclosure such as used for CSII therapy of diabetes mellitus. The ambulatory infusion device 10 has a housing 12 that includes a cartridge compartment 14 with a transparent window. The cartridge compartment 14 is designed to receive a cylindrical cartridge 50 of, for example, 3 ml or 300 I.U. (International Units) of insulin as maximum filling volume. From the cylindrical cartridge 50, insulin is infused by displacing a cartridge plunger in a controlled way via a dosing unit with a motor-operated spindle drive. The displacement of the spindle and the overall operation of the device are controlled by an electronic controller. The exemplary embodiment of the ambulatory infusion device further includes an input unit 18 in form of pushbuttons as well as a display 20. Further elements such as safety circuitry as well as data interfaces for remote controlling purposes and/or general data exchange purposes may additionally be present. The ambulatory infusion device 10 further includes a battery receiving portion for receiving an electrical battery in form of a replaceable battery (not visible in FIG. 1), which may or may not be rechargeable.

It should be understood that the design shown in FIG. 1 is meant to be exemplary. Several other designs and architectures for such devices are may be modified in accordance with the present disclosure as well.

Figure 2:
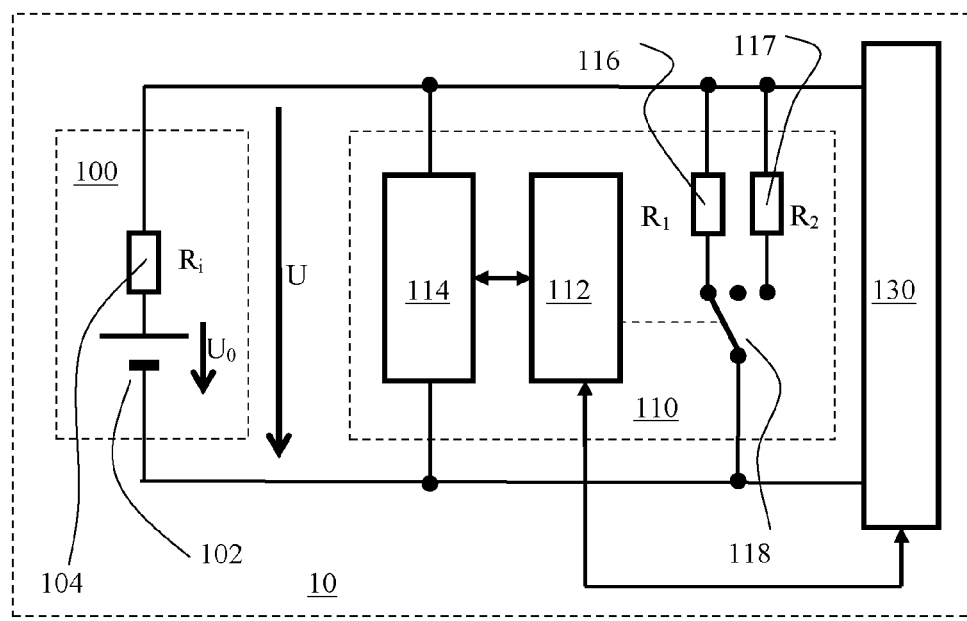
FIG. 2 shows an electrical diagram of a device in accordance with embodiments of the present disclosure.

FIG. 2 shows a schematic electrical diagram of the ambulatory infusion device 10 with battery 100. Battery 100 is a non-ideal battery which can be modeled in a simple model by an ideal battery 102 having an off-circuit voltage $U_0$ in series with an internal resistor 104 of resistance $R_i$ as described above. In an exemplary device, battery 100 may have a nominal voltage of 1.5V and be, for example, a standard AA or AAA cell. Other battery types having other nominal voltages may be used as well.

The ambulatory infusion device 10 further includes a testing unit 110. The testing unit 110 includes a test load in the form of two resistors 116, 117 of different resistances $R_1$ and $R_2$. Via an electronically controlled selector switch 118, either or none of the resistors 116, 117 can be coupled to the battery 100. Alternatively to different resistors 116, 117 and a selector switch 118, an electronically controlled resistor having a variable resistance, such as a voltage-controlled resistor, may be present.

The testing unit 110 further includes a voltage measurement unit 114 which is coupled to the terminals of the battery 100, thus measuring the terminal voltage U. The voltage measurement unit 114 has a substantially infinite input resistance that is especially much larger as compared to the resistances $R_1$ and $R_2$ such that the voltage measurement unit 114 does not significantly influence the measurements. Both the selector switch 118 and the voltage measurement unit 114 are activated and controlled via a control unit 112 which also controls the overall operation of the testing unit 110. The results of the voltage measurements are further evaluated by the control unit 112. In combination, the elements of the testing unit 110 allow determining the terminal voltage $U_0$ and the internal resistance $R_i$ of the battery 100.

Further circuitry of the ambulatory infusion device 10 is shown as combined in general circuitry 130. The general circuitry 130 includes in particular one or multiple controllers for controlling and supervising the device operation as well as a clock module, which activates the testing unit 110 in given testing intervals, thus triggering a test of the battery 100. The general circuitry 130 further includes the actuator of the dosing unit. The general circuitry further comprises an alerting unit with at least one of an acoustical or tactile indicator, such as a pager vibrator, that may be activated via the control unit 112.

It will be understood that FIG. 2 shows the testing unit 110 as separate from the general circuitry 130 for illustrative purposes only. In practice, the testing unit 110 may be combined with the general circuitry 130 fully or in part in any desired or favorable way. In particular, the control unit 112 and the voltage measurement unit 114 may be included in a microcontroller or the like, which also serves further purposes. The voltage measurement unit 114 may, for example, be based on an Analog-to-Digital-Converter, which is present in many microcontrollers. The same may hold true for further units such as the alerting unit and an optionally present prediction unit.

For carrying out a test, the control unit 112 controls the selector switch 118 to couple the test loads, which may be embodied as resistors 116 and 117 to the battery 100 in consecutive order and controls the voltage measurement unit 114 to measure the corresponding terminal voltages $U_1$, and $U_2$. Based on $U_1$ and $U_2$, the control unit 112 determines the internal resistance $R_i$ and the off-circuit voltage $U_0$ by applying Ohm's law in a straight-forward way. The accuracy of the computation increases with an increasing difference $\Delta R = |R_1 - R_2|$. In an exemplary device, $R_1$ may for example be 100Ω and $R_2$ may be 20Ω.

Figure 3:
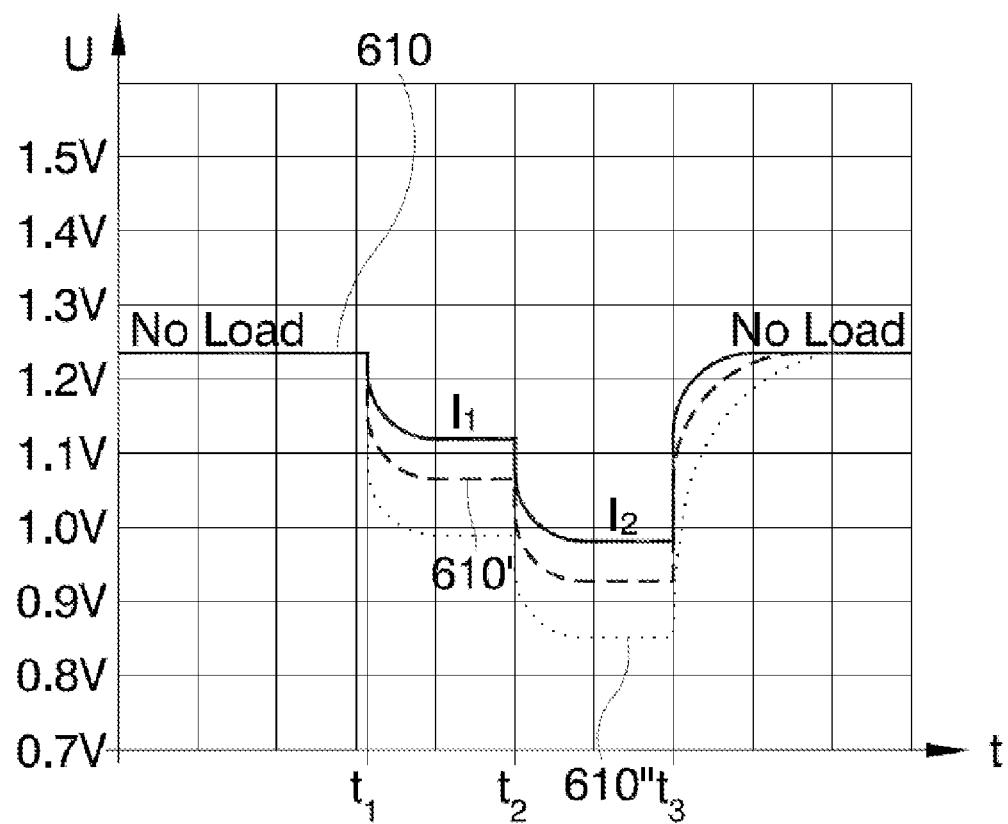
FIG. 3 shows the terminal voltage as function of time of batteries in different depletion states when consecutively coupled to two different test loads in accordance with embodiments of the present disclosure.
Figure 10:
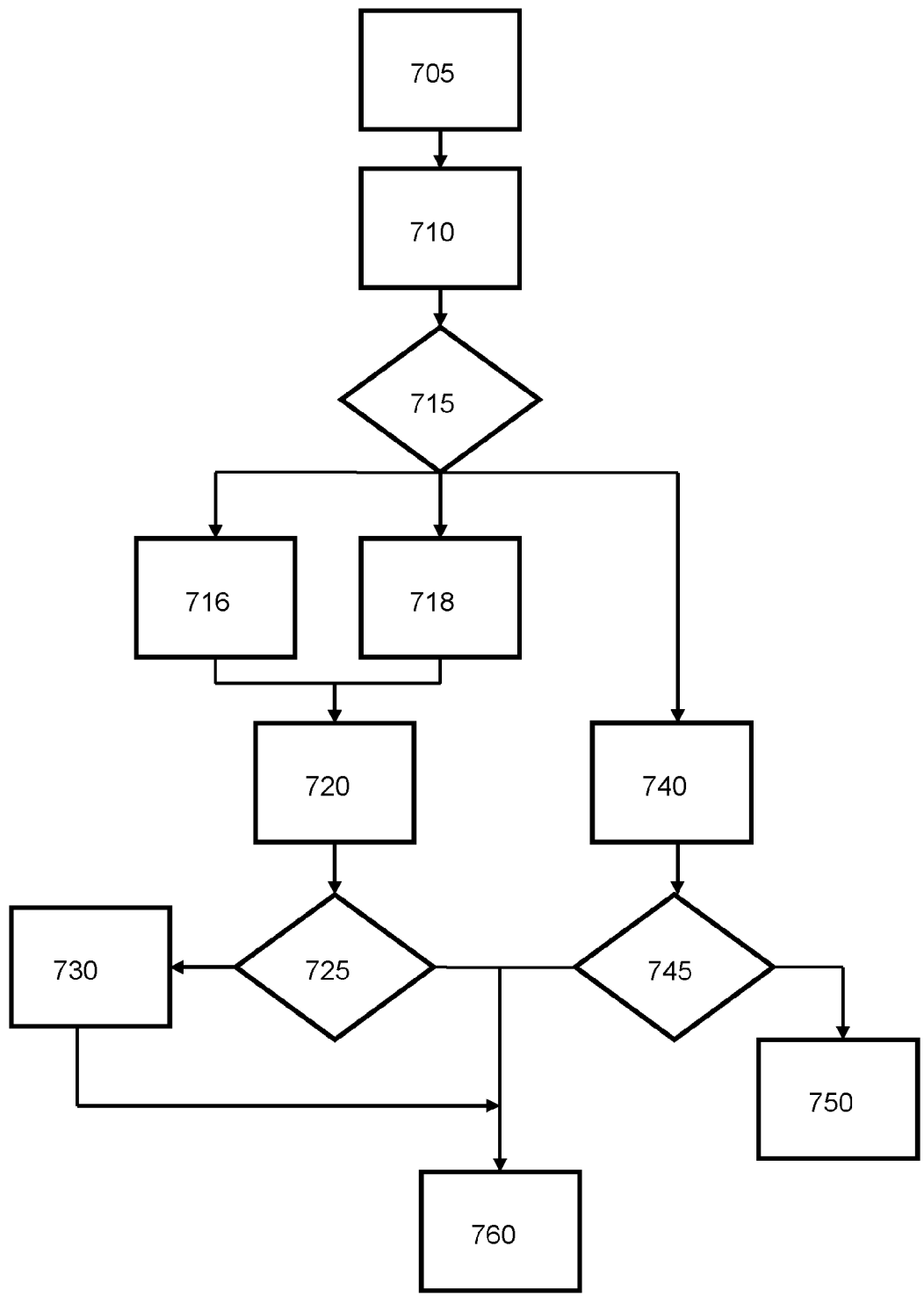
FIG. 10 shows the operational flow of assigning a battery type to a newly inserted battery in accordance with embodiments of the present disclosure.

FIG. 3 illustrates exemplary curves of the terminal voltage of the battery 100, with curve 610 being representative for a fresh or fully charged battery, curve 610' being representative for a partly depleted battery, and curve 610" for a largely depleted battery. The first portion of the graph, with $t<t_1$, shows the terminal voltage with substantially no current being drawn, such that it approximately equals the off-circuit voltage. For clarifying the effect of coupling the battery 100 to different test loads, the curves 610, 610', 610" are shown in FIG. 10 with equal off-circuit voltages. In practice, the off-circuit voltage for the partly exhausted battery (curve 610') may be somewhat lower as compared to the fresh battery (curve 610) and still lower for the largely exhausted battery (curve 610"), see also FIG. 4.

At $t=t_1$, the battery 100 is coupled to resistor 116 of resistance $R_1$, such that a current $I_1$ is drawn. Coupling the resistor 116 to the battery 100 causes a downwards step of the terminal voltage as step response. The different resulting terminal voltages are caused by the different internal resistances of the battery 100 as explained above. At $t=t_2$, the battery 100 coupled to resistor 117 of resistance $R_2$, resulting in a further downwards step of the terminal voltage. It is assumed that $R_2$ is smaller than $R_1$, resulting in a larger current, and, thus, a larger voltage drop over the internal resistor 104 of the battery 100 when connected to resistor 117. At $t=t_3$, resistor 117 is disconnected from the battery 100. The time interval from $t_1$ to $t_2$ and from $t_2$ to $t_3$ is typically in the range of some milliseconds.

It can be seen that the voltage drop over the internal resistor 104 increases with a decreasing test load resistance and increases with the usage time or grade of depletion of the battery. The decrease of the off-circuit voltage and the increase of the internal resistance are shown over the usage time of a battery in FIG. 4 as discussed above.

In dependence of the general circuitry 130 being modeled as a given-resistance device, a given-current device, or a given-power device, the testing unit 110 evaluates the corresponding criteria for determining whether the battery 100 is capable of further powering the ambulatory infusion device 10, as discussed above. The minimum operation voltage of the ambulatory infusion device 10 may, for example, be 0.8 V if the ambulatory infusion device 10 is powered by a standard AA or AAA cell. A maximum power consumption of the device is typically in a range of 0.5 W to 2 W but may also be smaller or larger in dependence of the device design.

It should be noted that determining the internal resistance $R_i$ does not require drawing the maximum current and/or power from the battery 100 that may be drawn during general device operation. Instead, the current and/or power that is drawn with either of the resistors 116 or 117 being coupled to the battery 100 may be considerably smaller as compared to the maximum current and/or power.

In some embodiments, the testing unit 110 carries out tests in a fixed testing interval of some minutes. Therefore, the testing unit 110 may comprise a dedicated timer. In some embodiments, the tests may be triggered via timers and/or clock circuitry of the general circuitry 130.

Figure 5:
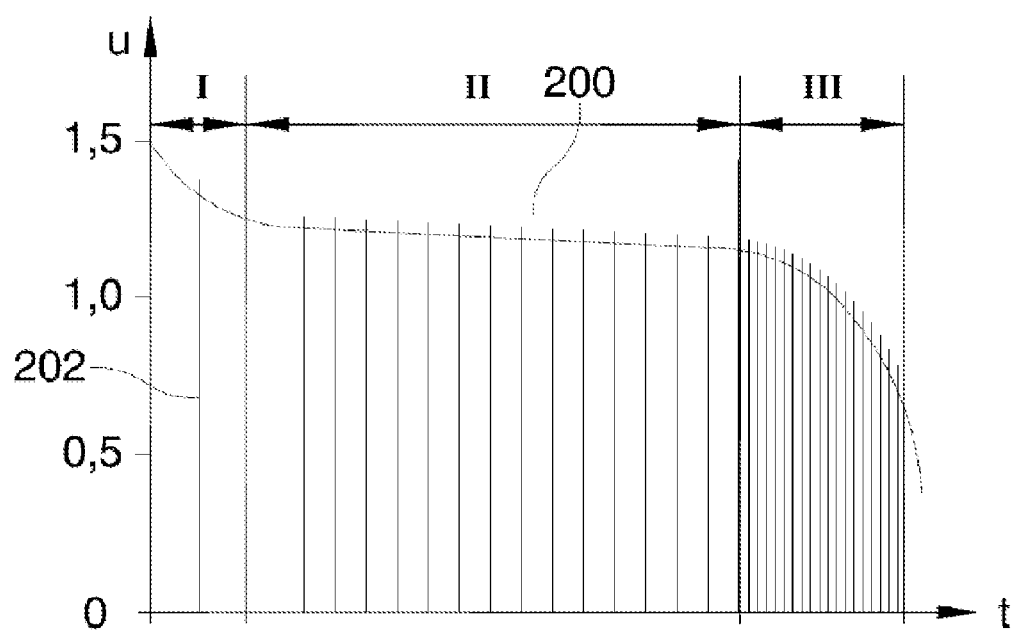
FIG. 5 shows a battery voltage of a device according to FIGS. 1 and 2 as a function of time along with the times for testing the battery for embodiments of the present disclosure.

Similarly, in some embodiments, the testing interval is not constant as will be described in the following with additional reference to FIG. 5. FIG. 5 shows a voltage curve 200 of the terminal voltage U of the battery 100 as a function of time t. The points in time where the battery 100 is tested are indicated by vertical lines 202. At those testing points in time, the voltage curve 200 shows the sampled terminal voltage U with either of the resistors 116 or 117 being coupled to the battery 100. Between the testing points in time, the voltage curve 200 is given by an interpolation of the sampled voltages.

The whole usage time of a battery, and, thus, the time span which is shown in FIG. 5, is typically in the range of some weeks, depending on the device design, the battery type and the use habits of the device user. While the voltage curve 200 holds qualitatively true for typical rechargeable as well as non-rechargeable batteries of different electro-chemical designs, the exact curve is different for different battery types and brands and additionally shows some battery-to-battery variation.

It can be seen that at the beginning, in an initial phase I, the voltage drop over time is rather large, followed by a long phase II where the voltage curve is almost horizontal, meaning the voltage drop over time is small. As the battery approaches the end of its useful lifetime in phase III, there is a steep voltage drop over time.

In the initial phase I, where the battery voltage is high, a comparatively long testing interval between consecutive tests is sufficient. In the main operation phase II, the testing interval is reduced. In the end phase III with a steep drop of the voltage over time, the testing interval is further reduced in order to ensure early detection of the end of the battery lifetime.

With $T_1$, $T_2$, $T_3$ being interval lengths and $U1$, $U2$ being threshold voltage levels for switching the testing intervals, the testing interval T is determined as $$T=T_1 \text{ for } U \geq U_1$$

$$T=T_2 \text{ for } U_1 > U \geq U_2$$

$$T=T_3 \text{ for } U < U_2 \quad (8).$$

For an Alkaline cell of 1.5V nominal voltage, the interval lengths may, for example be chosen as $T_1$=30 min, $T_2$=10 min, $T_3$=1 min. The threshold voltage levels may be chosen as $U_1$=1.3V and $U_2$=1.2V. The threshold voltage levels are favorably selected such that they approximately correspond to the transition from phase I to phase II and from phase II to phase III for a typical and non-defective battery. The voltage U that is used for evaluating (8) may be a terminal voltage for a given reference current, a terminal voltage for a given reference resistance or a terminal voltage for a given reference power drawn from the battery 100.

It should be noted that the number of three discrete interval lengths and two corresponding threshold voltage levels for switching between these testing intervals is exemplarily. Similarly, in some embodiments, a different number of k testing intervals, in particular a larger number, and k−1 corresponding threshold voltage levels may be used as well. Furthermore, the testing interval may be modified in a substantially continuous way. The testing interval may for example be as given by (8) for $U \geq U_1$ as well as for $U<U_2$ and may vary linearly with the voltage U in between.

Figure 6:
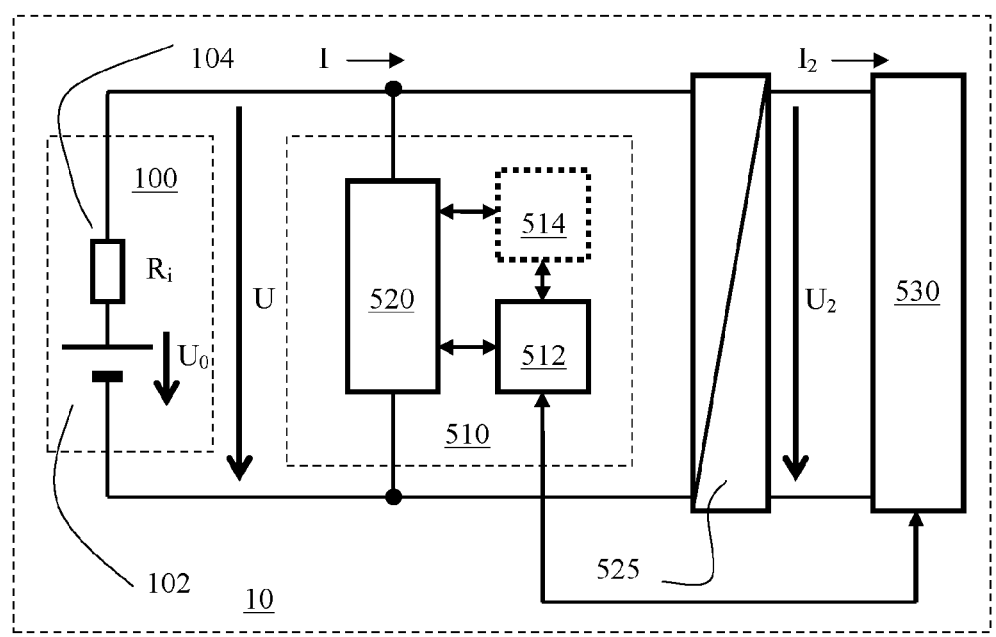
FIG. 6 shows an electrical diagram of a device in accordance with a further embodiments of the present disclosure.

In further embodiments, the testing interval may be varied in dependence with other variables such as the determined internal resistance of the battery. The schematic electrical diagram shown in FIG. 6 illustrates a further embodiment. This embodiment is different from the previously discussed embodiment in so far as the general circuitry 530 is not powered by the battery 100 directly but via a voltage converter 525. The voltage converter 525 may be configured as a DC/DC step-up converter which provides a constant output voltage $U_2$ for an input voltage being in a given range, with $U_2>U$, as described above. Since the output voltage of the voltage converter is maintained at a constant level, and the voltage converter 525 transforms the power from its input side to its output side according to (7), modeling the general circuitry as given-power device is appropriate in this case.

The testing unit 510 of this exemplary embodiment includes a control unit 512, a measurement unit 520 and an optional prediction unit 514 which is operatively coupled to the control unit 512 and the measurement unit 520. The measurement unit 520 and the control unit 512, in combination, are designed for determining the off-circuit voltage $U_0$ and the internal resistance $R_i$ of the battery 100.

The measurement unit may, for example, comprise a voltage measurement unit and two resistors that may alternatively be coupled to the battery 100 via a selector switch as well as additional components as shown and discussed in the context of FIG. 2. For determining if the battery is capable for powering the device, the testing unit 510 is designed to consider the following criteria: For determining if the terminal voltage U of the battery 100, and, thus, the input voltage of the voltage converter 525 is above the minimum operating voltage of the voltage converter 525, (5, 6) are evaluated in combination with (7). For determining if the required power can be drawn from the battery 100, (3) is evaluated.

Similarly, it is further considered if the maximum current that is drawn from the battery 100 during the device operation is below a maximum current that can be drawn from the battery and/or below a maximum input current of the voltage converter 525. The testing unit 510 is configured to activate an alerting unit that is comprised by the general circuitry if either or multiple of these criteria are not met.

Figure 7:
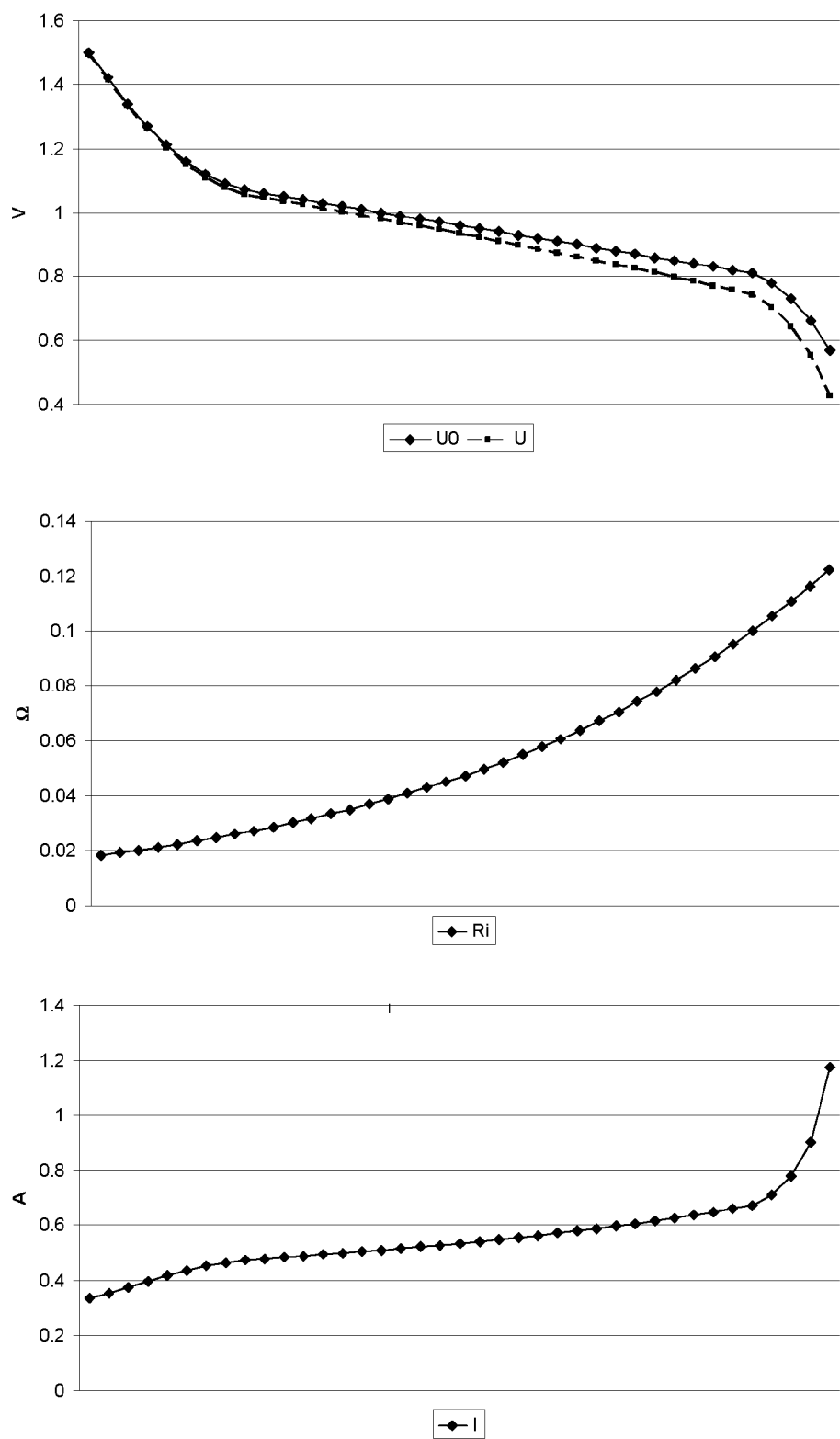
FIG. 7 shows an exemplary course of an off-circuit voltage a terminal voltage, an internal resistance and a current drawn from an exemplary battery over its usage time in accordance with embodiments of the present disclosure.

FIG. 7 shows a set of exemplary diagrams of some variables for a device in accordance with FIG. 6 for a power P=0.5 W drawn from an exemplary battery. One curve on FIG. 7 (*top*) shows the off-current voltage $U_0$ of an exemplary embodiment of the battery 100 with a nominal voltage of 1.5 V. This curve is qualitatively similar to the voltage curve 600 as shown in FIG. 4 and the voltage curve 200 as shown in FIG. 5. FIG. 7 (middle) shows the internal resistance $R_i$ of the battery as a function of time. This curve is qualitatively similar to the resistance curve 605 as shown in FIG. 4. FIG. 7 (bottom) shows the resulting current I that is drawn from the battery, and FIG. 7 (top) shows in a second curve the terminal voltage U as given by (5).

It can be seen that at the beginning the terminal voltage, U is almost identical to the off-circuit voltage $U_0$, resulting from a low internal resistance. As the internal resistance $R_i$ increases, the difference between the off-circuit voltage $U_0$ and the terminal voltage U increases. Both the decreasing off-circuit voltage $U_0$ as well as the increasing internal resistance $R_i$ cause the current I to increase over time for the drawn power being constant. The current increase, however, is moderate at the beginning. As the battery approaches the end of its usage time, the drawn current I increases steeply.

At the endpoints of the shown curves, the power P equals the maximum power that can be drawn from the battery according to (3). Beyond this point, the battery is not further capable for providing the required power. Here, the terminal voltage U, and, thus, the input voltage of the voltage converter 525 is about 0.4 V. If the minimum operating voltage of the voltage converter 525 is below this value, the maximum power that can be drawn from the battery according to (3) limits the capability of the battery for powering the device. If, however, the minimum operating voltage of the voltage converter 525 is higher, such as 0.6V or 0.7V, the battery is not capable for further powering the device when the terminal voltage drops below this voltage as given by (6), even though the required power could in principle be drawn from the battery. The testing unit may be designed to carry out tests with a fixed testing interval of, such as 3 minutes or with a variable testing interval as described above with reference to FIG. 5.

The testing unit 510 of the exemplary embodiment shown in FIG. 6 further comprises a prediction unit 514. Each time new values for the off-circuit voltage and the internal resistance have been determined, the prediction unit 514 predicts their future course via extrapolation as described above. Therefore, the testing unit 510 stores a set of previously determined values.

In some embodiments, instead of an extrapolation based on a set of determined values, the prediction unit 514 may store analytic functions that generally represent the course of the off-circuit voltage and the internal resistance, the functions having at least one adjustment parameter, and determine the at least one adjustment parameter to best fit the values that are determined via measurement. This approach, however, may fail in case of the battery being defective or showing an anomaly, such that the actual curves considerably deviate from what is expected for a normal battery.

Based on the predicted course of the off-circuit voltage and the internal resistance, the testing unit 510 is configured to activate the alerting unit if the prediction indicates that the battery will not be further capable for powering the device before expiration of a prediction interval of, for example, some hours according to any of the criteria discussed above. Alternatively or additionally to the off-circuit voltage and the internal resistance, the prediction unit 514 may predict the course of other variables that are derived from the off-circuit voltage and the internal resistance. The prediction unit 514 may, for example, directly predict the course of the current and the terminal voltage based on a set of previously determined values for these variables.

It should be noted that the prediction unit is favorable but not essential for the exemplary embodiments. In addition, while only shown and described in the context of the embodiment of FIG. 6, a prediction unit may also be present in other embodiments, such as shown in FIG. 2.

In addition or alternatively to monitoring the battery 100 during regular operation, the testing unit of any of the above-discussed embodiments may be used for carrying out one or more battery tests in the context of a power-up routine, following insertion of a battery into the device.

Figure 8:
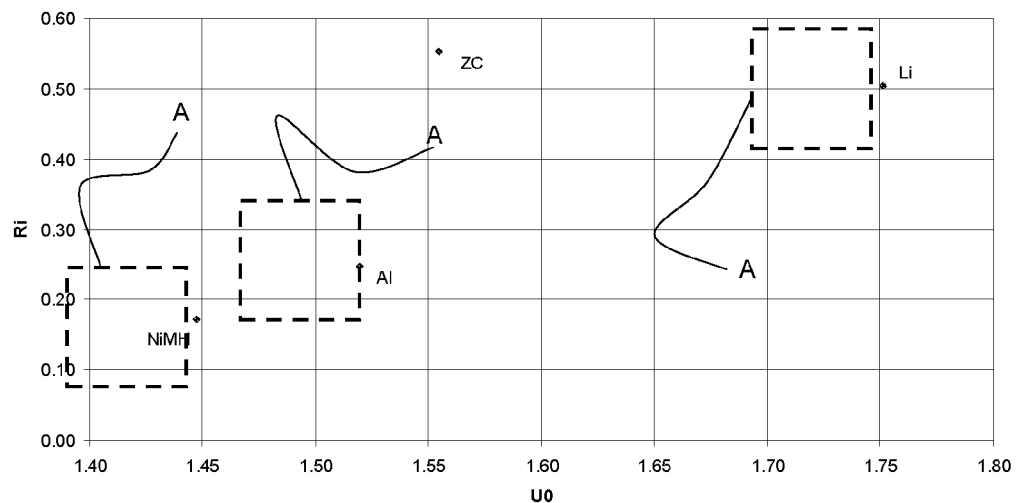
FIG. 8 shows the initial off-circuit voltage $U_0$ and the initial internal resistance $R_i$ in accordance with embodiments of the present disclosure.

FIG. 8 shows the off-circuit voltage $U_O$ and the internal resistance $R_i$ of different fresh general-purpose AA batteries, when connecting them successively to test loads of $39\Omega$ and $5\Omega$ for a time period in the milliseconds range. Corresponding values or ranges may be stored together with the battery type in a non-volatile memory of the device as initial values. From the measured terminal voltage for two different and known load resistances, the internal resistance $R_i$ and the off-circuit voltage $U_O$ can be determined by applying Ohm's law in a straight-forward way.

The areas A indicate exemplary value ranges for the off-circuit voltage and the internal resistance for the suited NIMH, AL, and LI batteries. The areas do not necessarily have the same size nor are they necessarily square. The size and shapes depend on the battery technologies and the expected variability of the parameters. Favorably, however, the areas A do not overlap for different battery types. A potential overlap results in the battery types not being clearly distinguishable. It may, however, be possible to allow a user selection between those battery types or to use worst-case values as described below. It is possible to define an area A also for batteries that are not suited for powering the device, for example, ZC batteries as described above, thus allowing clear identification. It is however, generally sufficient to detect in such a case that the inserted battery does not belong to any known and suited types.

Figure 9:
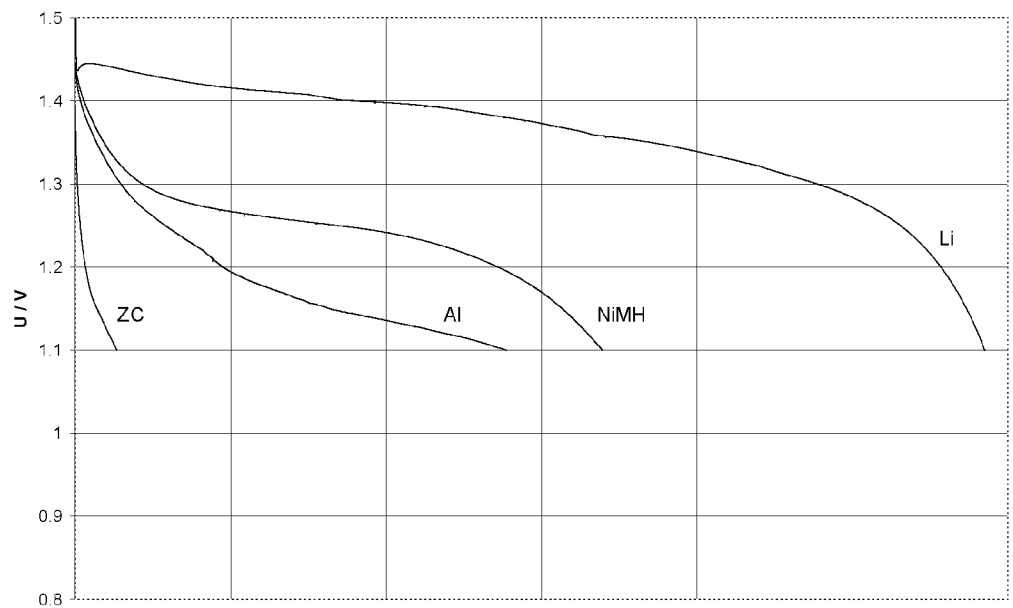
FIG. 9 shows the terminal voltage of different battery types as a function of time for accelerated discharging in accordance with embodiments of the present disclosure.

The diagram of FIG. 9 shows an example of the terminal voltage as a function of time for accelerated discharging of the batteries according to FIG. 8 at a constant load of 512, with the different curves being characteristic for the different battery designs. It can especially be seen that the Zinc-Carbon ZC battery shows a steep voltage decrease from the beginning on and drops very fast to a voltage level of 1.1V at which the discharging was stopped. Those characteristics result in ZC batteries being generally unsuited for reliably powering an infusion device.

FIG. 10 shows an operational flow following insertion of a battery into a device in accordance with the disclosure. The flow diagram is schematic to focus on the aspects of particular relevance in the present context. The blocks are carried out under control of the controller circuitry of the ambulatory infusion device. The blocks are favorably carried out in a stop, suspend, or maintenance mode that is different from a regular operation mode of the device and in which no drug is infused by the device.

In block 705, insertion of a battery is detected by the device. The following blocks are part of a power-up routine and are shown in FIG. 10 as being carried out substantially immediately after the battery insertion, but may also be carried out at another time during the power-up routine.

In block 710, the off-circuit voltage and the internal resistance of the battery are determined, as described above. In block 715, the determined values are compared with stored reverence values or value ranges for different battery technologies and the operational flow branches in dependence of the result.

In block 716 or block 718, a battery technology is assigned to the inserted battery. In addition, one or more threshold voltages are set in dependence of the battery technology. If no battery can be assigned, save worst-case values may be set or the battery may be rejected for operating the device as described with reference to block 740. The battery voltage falling below the threshold voltages causes the generation of an alert as described above during regular device operation. It should be noted that only two suited battery types are reflected in FIG. 10, which, however, may be extended to any number.

In block 720, the assigned battery technology is indicated to the device user via a display. In block 725, the user may confirm the assigned battery technology in which the operational flow proceeds with block 760, which may be a following block of the power-up routine or the switching into a regular operation mode of the device.

Similarly, from block 725, the user may override the automatic assignment and manually assign a battery technology in block 730, in which case the threshold voltage or voltages for alerting are modified in accordance with the manual setting. The option of manually overriding the automatic assignment may be useful in situations where the automatic assignment is, for any reason, not correct but the device user is sure about the battery technology.

If the comparison in block 715 shows that the battery is not suited for powering the device, that the battery is already largely depleted and/or no battery technology can be assigned, the operational flow branches to block 740 where a corresponding warning message is provided to the user. In block 745, the user may acknowledge the warning and the operational flow proceeds with block 750. Block 750 reflects a safe state from which the device can favorably not be switched into a regular operation mode. Alternatively, the user may decide in block 745 that the battery should be used anyhow, in which case the voltage thresholds for alerting are favorably set to a conservative (e.g., comparatively high) level and the operational flow proceeds with block 760 as described above. This option is useful in situations where no well-suited batteries are available.

Figure 11:
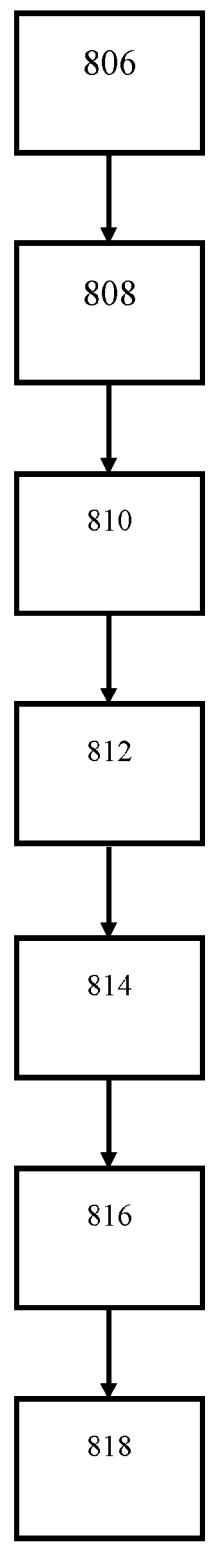
FIG. 11 shows the operational flow of an ambulatory infusion device following receipt of a newly inserted battery in accordance with embodiments of the present disclosure.

FIG. 11 shows operation flow of a process according to some embodiments disclosed herein. More specifically, as illustrated in block 806, the ambulatory infusion device 10 can receive insertion of a battery. At block 808, the ambulatory infusion device 10 can execute a power-up routine. At block 810, a determination can be made regarding an off-circuit voltage, as described above. At block 812, a determination can be made regarding an internal resistance of the battery. At block 814, a determination of a battery test result can be made from the off-circuit voltage and the internal resistance of the battery. At block 816, a determination of the capability of the battery for powering the ambulatory infusion device 10 can be made. At block 818, an alert may be provided to the user. The alert may be provided in response to a determination of a lack of capability of the battery to power the ambulatory infusion device 10 and/or for other reasons related to the battery test.

The invention claimed is:

1. A method for testing a battery of an ambulatory infusion device, the ambulatory infusion device being designed to be carried by a user external of a body, the battery being a user-replaceable battery of variable individual characteristics, the battery serving as primary power source of the ambulatory infusion device and which is successively depleted during application, the method comprising:
   determining an off-circuit voltage;
   determining an internal resistance of the battery,
   determining, from the off-circuit voltage and the internal resistance of the battery, a battery test result; and
   providing an alert to the user in dependence of the battery test result.

2. The method in accordance with claim 1, further comprising executing a power-up routine following insertion of the battery into a battery receiving portion of the ambulatory infusion device.

3. The method in accordance with claim 1, wherein the battery is tested during regular operation of the ambulatory infusion device, the method further comprising:
   determining, based on the off-circuit voltage and the internal resistance, a capability of the battery for powering the ambulatory infusion device; and
   providing the alert to the user in case of a lack of capability of the battery for powering the ambulatory infusion device.

4. The method in accordance with claim 2, further comprising storing a characteristic initial off-circuit voltage and a characteristic initial internal resistance for a number of different battery types and wherein the power-up routine includes assigning, based on a comparison of the characteristic initial off-circuit voltage and the characteristic initial internal resistance with the off-circuit voltage and initial resistance, a battery type to the battery.

5. The method in accordance with claim 4, further comprising providing an indication of the battery type to the device user.

6. The method in accordance with claim 2, further comprising providing the alert to the user if the battery test carried out during the power-up routine indicates that the battery is not suited for powering the ambulatory infusion device.

7. The method in accordance with claim 4, further comprising setting a predetermined threshold voltage in dependence of the battery type.

8. The method in accordance with claim 7, further comprising repeatedly determining the capability of the battery for further powering the ambulatory infusion device during regular operation of the ambulatory infusion device and providing the alert to the user if the voltage of the battery falls below the predetermined threshold voltage.

9. The method in accordance with claim 4, further comprising setting a predetermined threshold voltage in dependence of the battery type to a minimum operating voltage.

10. The method in accordance with claim 8, further comprising providing a warning a predetermined time before the battery falls below the predetermined threshold voltage, while the device is still operable.

11. The method in accordance with claim 3, further comprising determining the capability of the battery for powering the ambulatory infusion device by at least one of the following:
   determining if a terminal voltage of the user-replaceable battery exceeds a reference voltage,
   determining if a predetermined reference power can be drawn from the user-replaceable battery, and
   determining if a predetermined reference current can be drawn from the drawn from the user-replaceable battery.

12. The method in accordance with claim 1, wherein providing the alert is an acoustic signal, a tactile signal, an optical signal, or any combination thereof.

13. The method in accordance with claim 3, further comprising preventing the ambulatory infusion device from operating in a regular operation mode if the battery lacks capability for powering the ambulatory infusion device.

14. The method in accordance with claim 1, further comprising varying the determination of the off-circuit voltage and the internal resistance of the battery in dependence of the capability of the battery for further powering the ambulatory infusion device.

15. The method in accordance with claim 14, further comprising reducing the interval of the determination of the off-circuit voltage and the internal resistance of the battery upon a decreasing voltage.

16. The method in accordance with claim 14, further comprising reducing the interval of the determination of the off-circuit voltage and the internal resistance of the battery upon an increasing internal resistance of the battery.

* * * * *

UNITED STATES PATENT AND TRADEMARK OFFICE
CERTIFICATE OF CORRECTION

PATENT NO. : 8,936,572 B2
APPLICATION NO. : 13/826607
DATED : January 20, 2015
INVENTOR(S) : Thomas Rufer et al.

It is certified that error appears in the above-identified patent and that said Letters Patent is hereby corrected as shown below:

In the Specification

Col. 10, Line 52,
"$U = U_0 - R_i \cdot I$ (4),
$p = U \cdot I$"
should read
--$U = U_0 - R_i \cdot I$ (4),
$P = U \cdot I$--;

Col. 15, Line 36,
"T = $T_1$ for U ≥ $U_1$
T = $T_2$ for $U_1 >$ U ≥ U2 (8).
T = $T_3$ for U < $U_2$."
should read
--T = $T_1$ for U ≥ $U_1$
T = $T_2$ for $U_1 >$ U ≥ U$_2$ (8).
T = $T_3$ for U < $U_2$--;

Col. 18, Line 9,
"the batteries according to FIG. 8 at a constant load of 5Ω," should read
--the batteries according to FIG. 8 at a constant load of 5Ω,--;

Col. 5, Line 40,
"a time stamp. similar, the device may be configured to provide" should read
--a time stamp. Similarly, the device may be configured to provide--;

Signed and Sealed this
Nineteenth Day of January, 2016

Michelle K. Lee
*Director of the United States Patent and Trademark Office*

CERTIFICATE OF CORRECTION (continued)
U.S. Pat. No. 8,936,572 B2

Col. 6, Line 14,
"(NiMh), each of which may be identified by its initial off-" should read
--(NiMH), each of which maybe identified by its initial off- --;

Col. 11, Line 36,
"age to operate as specified, with the input volt$_a$ge of the" should read
--age to operate as specified, with the input voltage of the--;

Col. 13, Line 7,
"tures for such devices are may be modified in accordance with" should be
--tures for such devices maybe modified in accordance with--;

Col. 15, Line 30,
"With $T_1$, $T_2$, $T_3$ being interval lengths and U1, U2 being" should read
--With $T_1$, $T_2$, $T_3$ being interval lengths and $U_1$ $U_2$ being--;

Col. 17, Line 60,
"NIMH, AL, and LI batteries. The areas do not necessarily" should read
--NiMH, Al, and Li batteries. The areas do not necessarily--;

Col. 18, Line 34,
"reverence values or value ranges for different battery tech-" should read
--reference values or value ranges for different battery tech- --; and In the Claims Col. 20, Claim 11, Line 37,
"drawn from the drawn from the user-replaceable battery." should read
--drawn from the user-replaceable battery.--.